United States Patent [19]

Ramuz

[11] 4,366,160
[45] Dec. 28, 1982

[54] IMIDAZOLE DERIVATIVES

[75] Inventor: Henri Ramuz, Birsfelden, Switzerland

[73] Assignee: Hoffmann-La Roche Inc., Nutley, N.J.

[21] Appl. No.: 296,596

[22] Filed: Aug. 26, 1981

[30] Foreign Application Priority Data

Sep. 10, 1980 [CH] Switzerland .......... 6798/80
Jun. 24, 1981 [CH] Switzerland .......... 4175/81

[51] Int. Cl.³ .................. A61K 31/44; C07D 401/12
[52] U.S. Cl. .................. 424/263; 546/278; 548/316; 548/336
[58] Field of Search .......... 546/278; 424/263

[56] References Cited

U.S. PATENT DOCUMENTS

| | | | |
|---|---|---|---|
| 3,454,701 | 7/1969 | Zelle et al. | 424/273 |
| 3,872,121 | 3/1975 | Kummer et al. | 546/278 |
| 4,244,957 | 1/1981 | Ramuz | 424/263 |

FOREIGN PATENT DOCUMENTS

| | | |
|---|---|---|
| 623305 | 4/1963 | Belgium . |
| 687657 | 3/1967 | Belgium . |
| 721780 | 4/1969 | Belgium . |
| 721781 | 4/1969 | Belgium . |
| 2457979 | 6/1976 | Fed. Rep. of Germany . |
| 2709720 | 9/1978 | Fed. Rep. of Germany . |
| 6411516 | 4/1965 | Netherlands . |
| 6806606 | 11/1968 | Netherlands . |
| 6806672 | 11/1968 | Netherlands . |
| 1034938 | 7/1966 | United Kingdom . |

Primary Examiner—Norma S. Milestone
Attorney, Agent, or Firm—Jon S. Saxe; Bernard S. Leon; William G. Isgro

[57] ABSTRACT

Imidazole derivatives of the formula

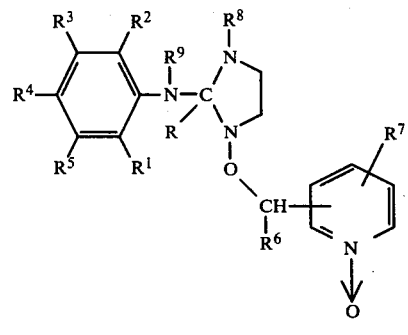

wherein $R^1$, $R^2$ and $R^3$, independently, are hydrogen, halogen, trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl(lower alkyl) or acyl and $R^9$ taken together with R is an additional bond, or $R^9$ is lower alkyl, lower alkenyl or aryl(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, and their pharmaceutically acceptable acid addition salts are described, the compounds of formula I have valuable therapeutic properties and are especially useful as analgesics.

24 Claims, No Drawings

IMIDAZOLE DERIVATIVES

BRIEF SUMMARY OF THE INVENTION

The invention relates to imidazole derivatives of the formula

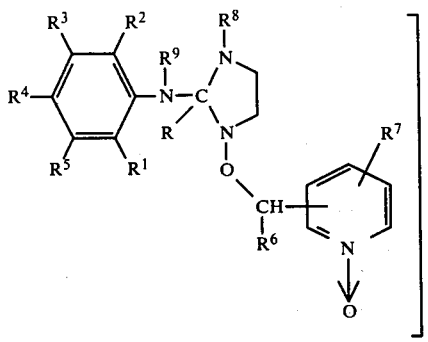

wherein $R^1$, $R^2$ and $R^3$, independently, are hydrogen, halogen, trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl-(lower alkyl) or acyl and $R^9$ taken together with R is an additional bond, or $R^9$ is lower alkyl, lower alkenyl or aryl-(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, and their pharmaceutically acceptable acid addition salts are described, the compounds of formula I are especially useful as analgesics.

In another aspect, the invention relates to intermediates for the preparation of the compounds of formula I.

In yet another aspect, the invention relates to pharmaceutical formulations containing the compounds of formula I.

In still another aspect, the invention relates to the use of the compounds of formula I as analgesics.

DETAILED DESCRIPTION OF THE INVENTION

The invention relates to imidazole derivatives of the formula

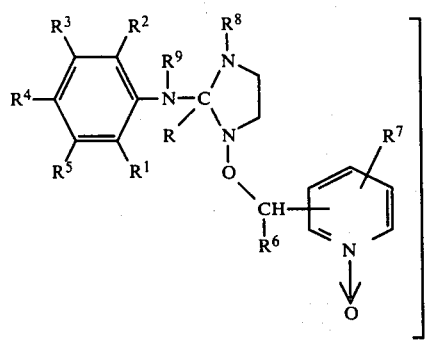

wherein $R^1$, $R^2$ and $R^3$, independently, are hydrogen, halogen, trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl-(lower alkyl) or acyl and $R^9$ taken together with R is an additional bond, or $R^9$ is lower alkyl, lower alkenyl or aryl-(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, and their pharmaceutically acceptable acid addition salts.

The compounds of formula I of the invention are distinguished by unexpectedly valuable pharmacological properties.

Objects of the present invention are imidazole derivatives of the formula I above and their pharmaceutically acceptable acid addition salts and the compounds of formula I as pharmaceutically active substances, the preparation of the compounds of formula I and intermediates for the preparation of said compounds, medicaments containing one or more compounds of formula I or pharmaceutically acceptable acid addition salts thereof, and the preparation of such medicaments, as well as the use of imidazole derivatives of formula I and of pharmaceutically acceptable acid addition salts thereof in the control or prevention of illnesses.

The compounds of formula I wherein $R^6$ is lower alkyl can exist in the (R)- or in the (S)-configuration or as a mixture of the two configurations. The invention encompasses not only the pure optical isomers, but also mixtures thereof, especially the corresponding racemates.

As used herein, the expression "lower alkyl", taken alone or in combinations such as in "lower alkylthio", "lower alkoxy" and the like, denotes straight-chain or branched-chain saturated hydrocarbon groups with at most 6, preferably at most 4, carbon atoms, for example, methyl, ethyl, n-propyl, isopropyl, isobutyl, n-butyl, t-butyl, amyl, hexyl and the like. The expression "lower alkylthio" denotes, for example, groups such as methylthio, ethylthio, n-propylthio, isopropylthio and the like. The expression "lower alkoxy" denotes, for example, groups such as methoxy, ethoxy, n-propoxy, isopropoxy and the like. The expression "halogen" denotes fluorine, chlorine, bromine or iodine. The expression "lower alkenyl" denotes straight-chain or branched-chain hydrocarbon groups with 2 to 6 carbon atoms in which at least one carbon-carbon bond is unsaturated, for example allyl, butenyl, isobutenyl and the like. The expression "aryl-(lower alkyl)" denotes, groups such as benzyl, phenethyl and the like. The expression "acyl" denotes lower alkanoyl, aroyl and aryl-(lower alkanoyl) groups, exemplary of which are formyl, acetyl, propionyl, butyryl, anisoyl, phenylacetyl and the like.

$R^1$, $R^2$ and $R^3$ preferably are, independently of one another, hydrogen, fluorine, chlorine, bromine, trifluoromethyl, methyl, ethyl or isopropyl. $R^4$ or $R^5$ preferably is hydrogen, chlorine, hydroxy or methoxy. $R^6$ preferably is hydrogen or methyl. $R^7$ preferably is hydrogen, hydroxy, methyl or methoxy. $R^8$ preferably is hydrogen, whereby $R^9$ taken together with R comprise an additional bond.

A preferred class of compounds of formula I are those in which $R^1$ or $R^3$ is hydrogen and $R^2$ and $R^3$ or $R^1$ and $R^2$ are the same, whereby $R^2$ and $R^3$ or $R^1$ and $R^2$ preferably are halogen and especially chlorine.

A more preferred class of compounds of formula I are those in which either $R^1$ and $R^2$ both are chlorine and $R^3$ is hydrogen, or $R^2$ and $R^3$ both are chlorine and $R^1$ is hydrogen, $R^4$, $R^5$ and $R^8$ are hydrogen and $R^9$ taken together with R comprise an additional bond.

A still more preferred compound provided by the invention is 2-([{2-[(2,6-dichlorophenyl)imino]-1-imidazolidinyl}oxy]methyl)pyridine-1-oxide.

Other more preferred compounds of formula I provided by the invention are:

2-([{2-[(2,3-Dichlorophenyl)imino]-1-imidazolidinyl}-oxy]methyl)pyridine-1-oxide;

2-[{[2-(2,6-dichloro-N-methylanilino)-2-imidazolin-1-yl]oxy}methyl]pyridine 1-oxide;

2-([{2-[(2,6-dichlorophenyl)imino]-1-imidazolidinyl}oxy]methyl)-4-methylpyridine 1-oxide;

4-(1-[{2-[(2,6-dichlorophenyl)imino]-1-imidazolidinyl}-oxy]ethyl)pyridine 1-oxide;

2-([{2-[(2,6-dichlorophenyl)imino]-1-imidazolidinyl}oxy]methyl)-5-methylpyridine 1-oxide;

2-([{2-[(2,6-dichlorophenyl)imino]-1-imidazolidinyl}oxy]methyl)-6-methylpyridine 1-oxide; and 2-([{2-[(2,6-dichlorophenyl)imino]-1-imidazolidinyl}oxy]methyl)-4-pyridinol 1-oxide.

The compounds of formula I above and their pharmaceutically acceptable acid addition salts can be prepared in accordance with the invention by (a) reacting a compound of the formula

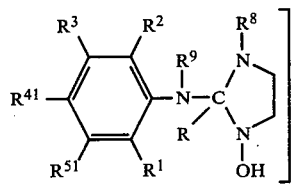

II wherein one of $R^{41}$ and $R^{51}$ is hydrogen and the other is hydrogen, halogen or lower alkoxy, and $R^1, R^2, R^3, R^8, R^9$ and R are as previously described, with a compound of the formula

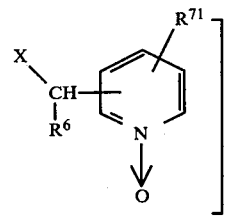

III wherein X is a leaving group and $R^{71}$ is hydrogen, lower alkyl or lower alkoxy, and $R^6$ is as previously described, or (b) acylating a compound of the formula

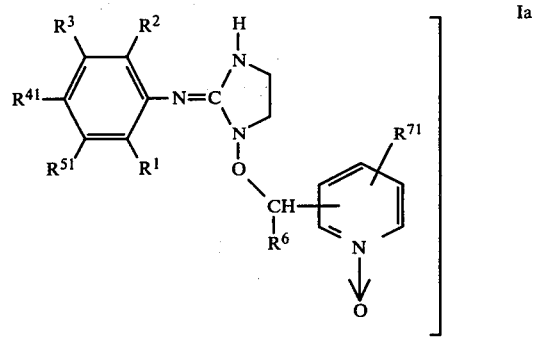

Ia wherein $R^1$, $R^2$, $R^3$, $R^{41}$, $R^{51}$, $R^6$ and $R^{71}$ are as previously described, at the secondary nitrogen atom, or (c) subjecting a compound of the formula

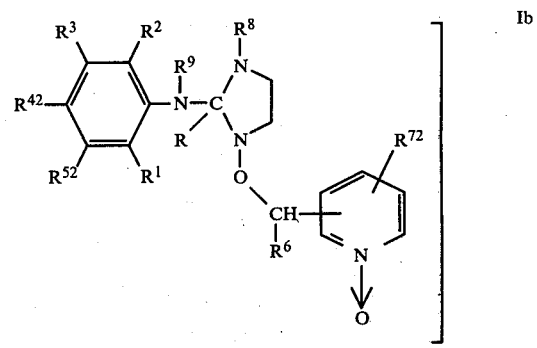

Ib wherein one of $R^{42}$ and $R^{52}$ is hydrogen and the other is lower alkoxy and $R^{72}$ is hydrogen, lower alkyl or lower alkoxy, or $R^{72}$ is lower alkoxy and one of $R^{42}$ and $R^{52}$ is hydrogen and the other is hydrogen, halogen or lower alkoxy, and $R^1$, $R^2$, $R^3$, $R^6$, $R^8$, $R^9$ and R are as previously described, to conditions suitable for ether cleavage, or (d) oxidizing a compound of the formula

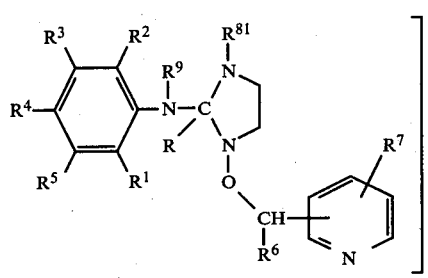

IV wherein either $R^{81}$ is lower alkyl, lower alkenyl, aryl-(lower alkyl) or acyl and $R^9$ taken together with R is an additional bond, or $R^9$ is lower alkyl, lower alkenyl or aryl-(lower alkyl) and $R^{81}$ taken together with R is an additional bond, and $R^1$, $R^2$, $R^3$, $R^4$, $R^5$, $R^6$ and $R^7$ are as previously described; provided that $R^4$ or $R^5$ is not hydroxy when $R^7$ is lower alkoxy and/or $R^{81}$ is acyl, and that $R^7$ is not hydroxy when $R^4$ or $R^5$ is lower alkoxy and/or $R^{81}$ is acyl, at the pyridine nitrogen atom, or (e) removing the acyl group in a compound of the formula

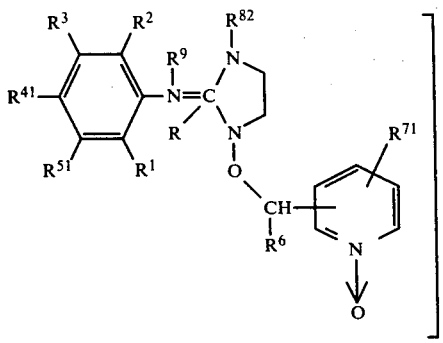

wherein $R^{82}$ is acyl, and $R^1$, $R^2$, $R^3$, $R^{41}$, $R^{51}$, $R^6$ and $R^{71}$ are as previously described, and (f) if desired, resolving a mixture of optical antipodes obtained, and (g) if desired, converting a compound of formula I into a pharmaceutically acceptable acid addition salt.

The reaction of a compound of formula II with a compound of formula III in which the leaving group denoted by X comprises known groups, for example, halogen, such as chlorine, bromine or iodine; aryl-sulfonyloxy such as p-toluenesulfonyloxy; alkylsulfonyloxy such as methanesulfonyloxy; and quaternary ammonium and sulfonium salts, can be carried out according to known methods. For example, a compound of formula II can be reacted with a compound of formula III in a two-phase system in the presence of a phase-transfer catalyst and a base. Suitable two-phase systems comprise, for example, water/toluene, water/benzene and the like. Preferred bases are sodium hydroxide, sodium carbonate, potassium carbonate or the like. Suitable phase-transfer catalyst are above all quaternary ammonium salts such as tetra-n-butylammonium sulfate, hydrogen sulfate, hydroxide and the like. For expediency, the reaction is preferably carried out at room temperature, although it can also be carried out readily at a temperature above or below room temperature.

The reaction of a compound of formula II with a compound of formula III can, however, also be carried out in an inert organic solvent such as dimethylformamide, dimethyl sulfoxide, tetrahydrofuran, diethyl ether, t-butyl methyl ether, toluene, xylene and the like in the presence of a base such as sodium hydride, potassium t-butylate and the like in a temperature range of from about $-50°$ C. to $100°$ C., preferably in the range of from about $20°$ C. to $45°$ C.

The acylation of a compound of formula Ia in accordance with process variant (b) can be carried out with any suitable acylating agent, for example, with a carboxylic acid anhydride such as acetic anhydride, benzoic acid anhydride or the like, according to known methods and which are familiar to any person skilled in the art.

The transformation of the lower alkoxy group(s) in a compound of formula Ib into hydroxy group(s) in accordance with process variant(c) is also carried out according to known methods. The desired ether cleavage is carried out, for example, with hydrochloric acid, hydrobromic acid or hydroiodic acid in aqueous or acetic acid solution at an elevated temperature, preferably at the boiling point of the reaction mixture, or with boron tribromide, boron trichloride or the like in an inert organic solvent such at pentane, benzene, toluene, methylene chloride and the like, at a temperature in the range of from about $0°$ C. to room temperature.

An acyl group which may be present in the molecule is also cleaved under the conditions described above.

The oxidation of a compound of formula IV at the pyridine nitrogen atom in accordance with process variant (d) can be carried out with various known oxidizing agents. Suitable oxidizing agents are above all peracids such as perbenzoic acid, m-chloroperbenzoic acid, peracetic acid or the like, hydrogen peroxide or alkyl hydroperoxides such as t-butyl hydroperoxide. Suitable solvents are, depending on the oxidizing agent used, alcohols such as methanol; halogenated hydrocarbons such as methylene chloride and chloroform; lower fatty acids such as formic acid, acetic acid and propionic acid; hydrocarbons such as benzene, toluene, cyclohexane and pentane; or the like.

The removal of the acyl group in a compound of formula Ic in accordance with process variant (e) is preferably carried out with an aqueous acid such as hydrochloric acid, hydrobromic acid, dilute sulfuric acid or the like, if desired in the presence of a solubilizing agent such as methanol, ethanol, tetrahydrofuran, dioxane or the like. Depending on the acid used, the reaction can be carried out at a temperature in the range of from about $0°$ C. to the boiling temperature of the reaction mixture.

The resolution of a mixture of optical antipodes obtained in accordance with process variant (f) is carried out according to known methods and which are familiar to any person skilled in the art. Such resolutions can be carried out, for example, via corresponding acid addition salts with optically active acids.

The compounds of formula I above can be converted into pharmaceutically acceptable acid addition salts, for instance, by treatment with an inorganic acid, for example, a hydrohalic acid such as hydrochloric or hydrobromic acid; sulfuric acid; phosphoric acid and the like; or with an organic acid, for example, tartaric acid; citric acid; methanesulfonic acid; cyclohexylaminosulfonic acid; and the like. A non-pharmaceutically acceptable acid addition salt of a compound of formula I can be converted in a known manner, for example, by treatment with alkali, into the free base and the resulting product, if desired, can be transformed into a pharmaceutically acceptable acid addition salt.

The compounds of formula II, in which $R^8$ is hydrogen and $R^9$ taken together with R is an additional bond, used as starting materials belong to a class of known substance. Specific representative compounds which have not previously been described can be prepared in analogy to the known compounds. Several of the examples hereinafter contain detailed information concerning the preparation of such compounds.

Compounds of formula II in which one of $R^8$ and $R^9$ is lower alkyl, lower alkenyl or aryl-(lower alkyl) and the other taken together with R is an additional bond form part of the invention and can be prepared by reacting a compound of the formula

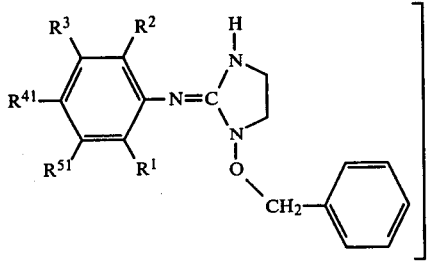

V wherein $R^1$, $R^2$, $R^3$, $R^{41}$ and $R^{51}$ are as previously described, with a compound of the formula $R^9-X$             VI or $R^{83}-X$           VII wherein $R^{83}$ is lower alkyl, lower alkenyl or aryl-(lower alkyl) and $R^9$ and X are as previously described. By suitable choice of the reaction conditions it is readily possible to carry out a selective alkylation of either the exocyclic nitrogen atom or the endocyclic nitrogen atom.

If the reaction is carried out under neutral or weakly basic conditions, for example, with sodium carbonate or potassium carbonate in an inert organic solvent such as methanol, ethanol, dimethylformamide, tetrahydrofuran, dioxane or the like, or in a two-phase system in the presence of a phase-transfer catalyst, if desired with the addition of a weak base, then the exocyclic nitrogen atom can be alkylated selectively with a compound of formula VI.

On the other hand, if a compound of formula V is treated with a strong base such as sodium hydride in an inert solvent such as dimethylformamide, tetrahydrofuran, dioxane or the like, then there is obtained the corresponding anion which is alkylated at the endocyclic nitrogen atom by a compound of formula VII.

A compound that is obtained by such procedure corresponds to the formula

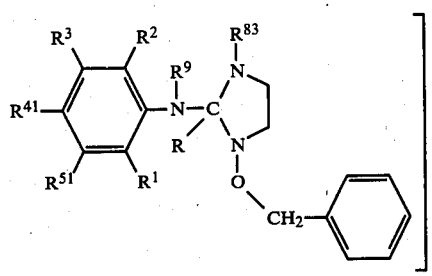

VIII wherein one of $R^{83}$ and $R^9$ is lower alkyl, lower alkenyl or aryl-(lower alkyl) and the other taken together with R is an additional bond, and $R^1$, $R^2$, $R^3$, $R^{41}$ and $R^{51}$ are as previously described. The benzyl group can be cleaved from a compound of formula VIII above by treatment with a hydrohalic acid, preferably hydrobromic acid, or with a Lewis acid such as boron trichloride in an inert solvent such as methylene chloride at temperatures in the range of from about −60° C. to 0° C., or with hydrogen in the presence of a catalyst such as platinum oxide, palladium or palladium/carbon in a solvent such as ethanol, methanol, acetic acid, water or mixtures thereof, if desired with the addition of a mineral acid such as hydrochloric acid. Of course, there should be used only those reaction conditions which do not interfere in an undesirable manner with other structural elements present in the molecule. By this process, there is obtained a compound of the formula

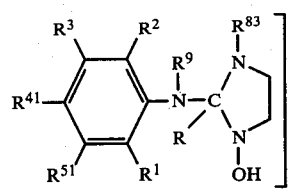

IIa wherein $R^1$, $R^2$, $R^3$, $R^{41}$, $R^{51}$, $R^{83}$, $R^9$ and R are as previously described.

Compounds of formula II in which $R^8$ is acyl can be prepared by removing the benzyl group in a compound of formula V as described above and acylating a thus-obtained compound of the formula

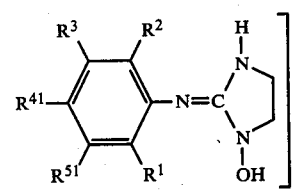

IX wherein $R^1$, $R^2$, $R^3$, $R^{41}$ and $R^{51}$ are as previously described, at the secondary nitrogen atom. This acylation can be carried out with any suitable acylating agent, for example, with an anhydride such as acetic anhydride or benzoic acid anhydride; or an acid chloride such as acetyl chloride or phenylacetic acid chloride. Suitable reaction conditions can be ascertained readily by any person skilled in the art.

The compounds of formula V belong to a class of known substance. Specific representative compounds which have not previously been described can be prepared in a known manner, that is, in a manner analogous to the preparation of the known representatives.

The compounds of formula IV used as starting materials can be prepared, for example, starting from compounds of the formula

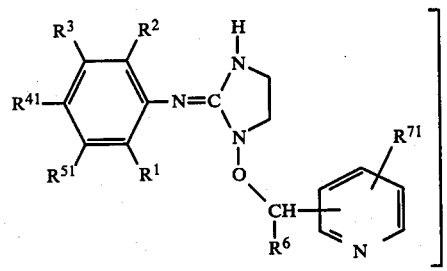

X wherein $R^1$, $R^2$, $R^3$, $R^{41}$, $R^{51}$, $R^6$ and $R^{71}$ are as previously described, which are known or can be prepared according to known methods. For example, a compound of formula X can be reacted with a reactive derivative of a carboxylic acid, for example, with an anhydride such as acetic anhydride, benzoic acid anhydride and the like; or with an acid chloride such as acetyl chloride and benzoyl chloride or the like; or with formic acid and acetic anhydride. There is thus obtained a compound of the formula

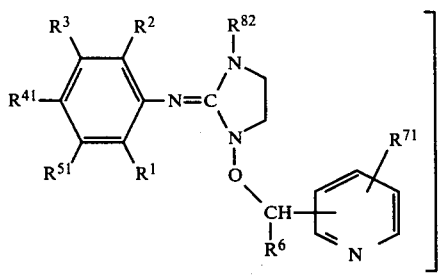

wherein $R^1$, $R^2$, $R^3$, $R^{41}$, $R^{51}$, $R^6$, $R^{71}$ and $R^{82}$ are as previously described.

Furthermore, it is possible to react a compound of formula IIa, in analogy to process variant (a), with a compound of the formula

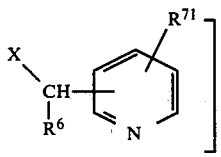

wherein X, $R^6$ and $R^{71}$ are as previously described, and obtain a compound of the formula

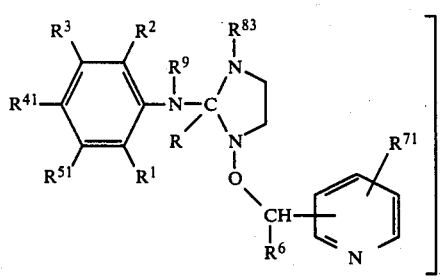

wherein $R^1$, $R^2$, $R^3$, $R^{41}$, $R^{51}$, $R^6$, $R^{71}$, $R^{83}$, $R^9$ and R are as previously described.

Compounds of formula IV in which $R^4$ or $R^5$ and/or $R^7$ is hydroxy can be obtained from compounds of formula IVb in which $R^{41}$ or $R^{51}$ and/or $R^{71}$ is lower alkoxy in analogy to process variant (c).

The compounds of formula II in which $R^8$ is not hydrogen and the compounds of formula IV used as starting materials also form part of the invention.

As mentioned earlier, the imidazole derivatives of formula I in accordance with the invention are distinguished by valuable pharmacological properties. In particular, they exhibit analgesic activity and accordingly can be used as analgesics in the control or prevention of pains.

The analgesic properties of the compounds of formula I can be demonstrated with the writhing test described hereinafter:

In carrying out the experiment there are used in each case 8 male mice (20–22 g) per dosage. 60 minutes after the oral administration of the test substance 10 ml/kg of the test solution is administered to the animals by intraperitoneal injection. After a latent period of 5 minutes, the number of animals in which during 5 minutes no more than one characteristic writhing symptom, that is, convulsive stretching movement of the body, occurs is registered. The ED 50 indicates the oral dosage in mg/kg at which 50% of the animals show no more than one writhing.

A. 2-([{2-[(2,6-Dichlorophenyl)imino]-1-imidazolidinyl}oxy]methyl)pyridine 1-oxide.
B. 2-([{2-[(2,3-Dichlorophenyl)imino]-1-imidazolidinyl}oxy]methyl)pyridine 1-oxide.
C. 2-[{[2-(2,6-Dichloro-N-methylanilino)-2-imidazolin-1-yl]oxy}methyl]pyridine 1-oxide.
D. 2-([{2-[(2,6-Dichlorophenyl)imino]-1-imidazolidinyl}oxy]methyl)-4-methylpyridin 1-oxide.
E. 4-(1-[{2-[(2,6-Dichlorophenyl)imino]-1-imidazolidinyl}oxy]ethyl)pyridine 1-oxide.
F. 2-([{2-[(2,6-Dichlorophenyl)imino]-1-imidazolidinyl}oxy]methyl)-5-methylpyridin 1-oxide.
G. 2-([{2-[(2,6-Dichlorophenyl)imino]-1-imidazolidinyl}oxy]methyl)-6-methylpyridin 1-oxide.
H. 2-([{2-[(2,6-Dichlorophenyl)imino]-1-imidazolidinyl}oxy]methyl)-4-pyridinol 1-oxide.

| Writhing Test (mouse) 60 minutes after peroral administration | |
|---|---|
| | $ED_{50}$ in mg/kg (orally) |
| A | 3.5 |
| B | 1.3 |
| C | 26.0 |
| D | 16.0 |
| E | 7.3 |
| F | 27.0 |
| G | 16.0 |
| H | 8.7 |

Compound A brings about in apes, after peroral administration, a three-times stronger activity than morphine against an electrical stimulation of the dental pulp. On the contrary, no morphine-antagonistic activity could be found, from which the absence of an addictive activity can be concluded. The analgesia produced by compound A can be cancelled out with the α-adrenergic receptor blocker yohimbine, but not with the opiate receptor blocker naloxone. This fact indicates that the analgesia is produced via a mechanism independent of opiate receptors.

Surprisingly, it has been found that the imidazole derivatives of formula I of the invention, in contrast to other pharmaceutically active imidazole derivatives, have no, or at most minimum, cardiovascular activities, and no central sympathetic-inhibitory activity.

The cardiovascular activities can be determined according to the following method:

The systolic blood pressure and the heart rate are measured several times on conscious, spontaneously hypertensive female rats before the administration of the subtance. Per dosage there are used 5 experimental animals with a body weight of about 300 g. The administration of substance is carried out by means of a stomach probe. Both parameters are measured 1, 3, 6 and 16 hours after the administration and the percentage variation from the control values is calculated. The systolic blood pressure is measured indirectly at the tail artery of the rate according to the method of Gerold et al. (Helv. Physiol. Acta 24, 58–69 (1966); Arzneimittelforschung 18, 1285–1287 (1968).

The central sympathetic-inhibitory activity can be determined according to the following method:

The action of the test compounds on the activity in the sympathetic nervous system is investigated on cats in urethane narcosis. The preganglionic sympathetic activity is derived by means of biopolar platinum electrodes from the splanchnic nerve and the postganglionic sympathetic activity is derived from a nerve branch to the kidney according to the method of G. Häusler [Naunyn-Schmiedeberg's Arch. Pharmacol. 286, 97-111 (1974)]. Moreover, there is measured the arterial blood pressure from the femoral artery as well as the heart rate. The test substance is injected intravenously. When a test substance in blood pressure-lowering dosages inhibits the sympathetic activity during more than 30 minutes by more than 30%, then it is qualified as having "central sympathetic-inhibitory activity".

In the Table which follows, the results obtained with compounds A to H are compiled. The maximum percentage variations from the control values are given.

|  | Anaesthetized cat | | | Central sympathetic-inhibitory activity | Spontaneously hypertensive rat | | |
|---|---|---|---|---|---|---|---|
| Compound | Dosage in mg/kg (i.v.) | Blood pressure, Δ% | Heart rate, Δ% | | Dosage in mg/kg (p.o.) | Blood pressure, Δ% | Heart rate, Δ% |
| A | 1.0 | −5 | −5 | none | 1.0 | −0.2 | +15.2 |
|   | 3.0 | −10 | −5 |      | 3.0 | +0.3 | +3.3 |
|   | 10.0 | −10 | −29 |     | 10.0 | −3.1 | −9.6 |
|   |      |     |     |     | 30.0 | −10.5 | −3.6 |
|   |      |     |     |     | 100.0 | 0 | 0 |
| B | 1.0 | −5 | 0 | none | 1.0 | −4.1 | −11.8 |
|   | 3.0 | −25 | −6 |     | 3.0 | −7.8 | −8.4 |
|   | 10.0 | −50 (15') | −6 | | | | |
| C | 1.0 | −14 (5') | −6 | none | 1.0 | +0.3 | +6.3 |
|   | 3.0 | −21 (10') | −22 (10') | | 3.0 | +1.2 | −5.8 |
|   | 10.0 | −21 (10') | −22 (10') | | 10.0 | +2.2 | +3.2 |
| D | 1.0 | −22 (3') | −9 | none | 1.0 | −7.0 | −10.0 |
|   | 3.0 | −22 | −27 |     | 3.0 | −10.2 | −7.5 |
|   |      |     |     |     | 10.0 | −12.6 | −13.3 |
| E | 1.0 | 0 | 0 | none | 3.0 | +10.2 | +4.0 |
|   | 3.0 | −4 | 0 |      | 10.0 | −13.9 | −13.2 |
|   | 10.0 | −12 | −14 |    | 30.0 | +2.4 | −9.9 |
| F | 1.0 | 0 | 0 | none | 1.0 | −9.6 | −4.9 |
|   | 3.0 | 0 | 0 |       | 3.0 | −10.4 | −5.5 |
|   | 10.0 | 0 | −10 |    |     |     |     |
| G | 1.0 | −4 | 0 |      | 10.0 | −12.0 | −22.6 |
|   | 3.0 | −4 | −4 | none |     |     |     |
|   | 10.0 | −15 | −13 |    |     |     |     |
| H | 1.0 | −12 | 0 |      |     |     |     |
|   | 3.0 | −27 (10') | −2 | none | | | |
|   | 10.0 | −62 (10') | −18 (10') | | | | |

The compounds of formula I of the invention and their pharmaceutically acceptable acid addition salts can be used as medicaments, for example, in the form of pharmaceutical preparations which contain them or their salts in admixture with a pharmaceutically inert, organic or inorganic, carrier material suitable for enteral or parenteral administration such as, for example, water, gelatin, gum arabic, lactose, starch, magnesium stearate, talc, vegetable oils, polyalkyleneglycols, and the like. The pharmaceutical preparations can be made up in a solid form, for example, as tablets, dragees, suppositories or capsules, or in a liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The daily dosage in the case of oral administration is in the range of from about 1 to 200 mg and in the case of intravenous administration is in the range of from about 0.1 to 20 mg. These dosages are, however, only given by way of example and can be altered depending on the severity of the condition and according to the needs of the warm-blooded animal.

As mentioned earlier, medicaments containing a compound of formula I of the invention or a pharmaceutically acceptable acid addition salt thereof are also an object of the invention, as is a process for the preparation of such medicaments which is characterized by combining one or more compounds of formula I or pharmaceutically acceptable acid addition salts thereof and, if desired, one or more other therapeutically valuable substances into a galenical form. Another object of the invention is, as mentioned earlier, the use of compounds of formula I and their pharmaceutically acceptable acid addition salts in the control or prevention of illnesses, especially in the control or prevention of pains.

The Examples which follow further illustrate the invention. All temperatures are given in degrees Centigrade. The melting points are not corrected.

EXAMPLE 1

Preparation of 2-([{2-[(2,6-dichlorophenyl)imino]-1-imidazol idinyl}oxy]methyl)-pyridine 1-oxide A suspension of 9.84 g of 2-[(2,6-dichlorophenyl)imino]-1-hydroxyimidazolidine, 1.4 g of tetra-n-butylammonium sulfate and 7.56 g of 2-chloromethyl-pyridine N-oxide hydrochloride in 140 ml of toluene is treated with 30 ml of 28 percent sodium hydroxide while stirring vigorously. The temperature rises immediately to 30°. After 2 hours, the precipitate is removed by filtration under suction, washed with water and dried at 60° in vacuo. From methanol and acetonitrile there is obtained 2-([{2-[(2,6-dichlorophenyl)imino]-1-imidazol idinyl}oxy]methyl)-pyridine 1-oxide of melting point 185°-187°. The corresponding hydrochloride crystallizes from methanol/acetonitrile with 2.5 mol of hydrochloric acid and melts at 171°-173°. The corresponding cyclohexylsulfamate decomposes slowly from 159°–238°.

EXAMPLE 2

The following compounds are prepared in analogy to the details in Example 1:

From 2-[(2,6-dichlorophenyl)imino]-1-hydroxyimidazolidine and 3-chloromethyl-pyridine N-oxide there is obtained 3-([{2-[(2,6-dichlorophenyl)imino]-1-imidazolidinyl}oxy]methyl) pyridine 1-oxide dihydrochloride of melting point 199°–200° (methanol/acetone);

from 2-[(o-chlorophenyl)imino]-1-hydroxyimidazolidine and 2-chloromethyl]-pyridine N-oxide there is obtained 2-([{2-[(o-chlorophenyl)imino]-1-imidazolidinyl}-oxy]methyl)pyridine 1-oxide hydrobromide of melting point 166°–167° (acetone/methanol);

from 2-[(2,6-dichlorophenyl)imino]-1-hydroxyimidazolidine and 3-[1-chloroethyl]-pyridine N-oxide there is obtained 3-(1-[{2-[(2,6-dichlorophenyl)imino]-1-imidazolidinyl}oxy]ethyl)-pyridine 1-oxide hydrobromide of melting point 271°–272° (acetone/30 percent hydrogen bromide in glacial acetic acid);

from 1-hydroxy-2-(phenylimino)imidazoline and 2-chloromethyl-pyridine N-oxide there is obtained 2-[{[2-(phenylimino)-1-imidazolidinyl]oxy}methyl]-pyridine 1-oxide dihydrobromide of melting point 173° (acetone/30 percent hydrogen bromide in glacial acetic acid) with decomposition;

from 2-[(2,6-dichlorophenyl)imino]-1-hydroxyimidazolidine and 4-(1-chloroethyl)-pyridine N-oxide there is obtained 4-(1-[{2-[(2,6-dichlorophenyl)imino]-1-imidazolidinyl}oxy]ethyl)-pyridine 1-oxide dihydrobromide of melting point 232°–233°;

from 2-[(2,6-dichlorophenyl)imino]-1-hydroxyimidazolidine and 4-methyl-2-chloromethyl-pyridine N-oxide there is obtained 2-([{2-[(2,6-dichlorophenyl)-imino]-1-imidazolidinyl}oxy]methyl)-4-methyl-pyridine 1-oxide of melting point 181° (methanol/acetonitrile);

from 2-[(2,6-dichlorophenyl)imino]-1-hydroxyimidazolidine and 5-methyl-2-chloromethyl-pyridine N-oxide there is obtained 2-([{2-[(2,6-dichlorophenyl)-imino]-1-imidazolidinyl}oxy]methyl)-5-methyl-pyridine 1-oxide of melting point 201°–202° (acetonitrile);

from 2-[(2,6-dichlorophenyl)imino]-1-hydroxyimidazolidine and 2-(1-chloroethyl)pyridine N-oxide there is obtained 2-(1-[{2-[(2,6-dichlorophenyl)imino]-1-imidazolidinyl}oxy]ethyl)-pyridine-1-oxide dihydrobromide of melting point 176°–177° (acetone/methanol);

from 1-hydroxy-2-[(α,α,α-trifluoro-m-tolyl)imino]-imidazolidine and 2-chloromethyl-pyridine N-oxide there is obtained 2-([{2-[(α,α,α-trifluoro-m-tolyl)imino]-1-imidazolidinyl}oxy]methyl)-pyridine 1-oxide of melting point 95°–97° (isopropyl ether);

from 2-[(2,3-dichlorophenyl)imino]-1-hydroxyimidazolidine and 2-chloromethyl-pyridine N-oxide there is obtained 2-([{2-[(2,3-dichlorophenyl)imino]-1-imidazolidinyl}oxy]methyl) pyridine 1-oxide of melting point 168°–169° (acetonitrile);

from 1-hydroxy-2-[(α,α,α-trifluoro-o-tolyl)imino]-imidazolidine and 2-chloromethyl-pyridine N-oxide there is obtained 2-([{2-[(α,α,α-trifluoro-o-tolyl)imino]-1-imidazolidinyl}oxy]methyl)pyridine 1-oxide of melting point 175°–176° (methanol/acetone);

from 2-(o-cumenylimino)-1-hydroxyimidazolidine and 2-chloromethyl-pyridine N-oxide there is obtained 2-[{[2-(o-cumenylimino)-1-imidazolidinyl]oxy}methyl]pyridine 1-oxide of melting point 136°–137° (acetone/isopropyl ether);

from 2-[(2,5-dichlorophenyl)imino]-1-hydroxyimidazolidine and 2-chloromethyl-pyridine N-oxide there is obtained 2-([{2-[(2,5-dichlorophenyl)imino]-1-imidazolidinyl]oxy}methyl)pyridine 1-oxide of melting point 167°–168° (acetonitrile);

from 1-hydroxy-2-(2,6-xylylimino)imidazolidine and 2-chloromethyl-pyridine N-oxide there is obtained 2-([{2-[(2,6-xylyl)imino]-1-imidazolidinyl}oxy]methyl)pyridine 1-oxide of melting point 118°–120° (ether);

from 2-[(2,4-dichlorophenyl)imino]-1-hydroxyimidazolidine and 2-chloromethyl-pyridine N-oxide there is obtained 2-([{2-[(2,4-dichlorophenyl)imino]-1-imidazolidinyl}oxy]methyl)pyridine 1-oxide of melting point 168°–169° (chloroform/ethanol);

from 2-[(2,6-dibromophenyl)imino]-1-hydroxyimidazolidine and 2-chloromethyl]-pyridine N-oxide there is obtained 2-([{2-[(2,6-dibromophenyl)imino]-1-imidazolidinyl}oxy]methyl)pyridine 1-oxide of melting point 163°–165° (ethanol).

EXAMPLE 3

Preparation of 2-([{2-[(2,6-difluorophenyl)imino]-1-imidazolidinyl}oxy]methyl)-pyridine 1-oxide dihydrochloride (a) A solution of 19.68 g of 2,6-difluorophenylisothiocyanate and 34.1 g of N-{2-[N-(benzyloxy)amino]ethyl}phthalimide in 150 ml of benzene is heated to boiling under reflux for 6 hours. The cooled solution is separated from a slight precipitate and then evaporated in vacuo. The residual oil crystallizes from isopropyl ether. There is obtained 1-(benzyloxy)-3-(2,6-difluorophenyl)-1-(2-phthalimidoethyl)-2-thiourea of melting point 141°–143° (ether/methylene chloride).

(b) 30.1 g of the thus-obtained substance are stirred overnight with 300 ml of a 40 percent methylamine solution. Subsequently, the solution is held at 50° for 1 hour, cooled down to 10° and extracted with ether. The organic phase is extracted three times with a 15 percent tartaric acid solution. The aqueous extract is subsequently made basic with concentrated ammonia and extracted with ether. The ethereal extracts are dried and evaporated in vacuo. The residual oil is used in the next step without further purification. The 1-(benzyloxy)-2-[(2,6-difluorophenyl)imino]imidazolidine hydrochloride melts at 159°–160° (acetone).

(c) 16.0 g of the above substance are heated to 150° with 100 ml of 48 percent hydrobromic acid. After 30 minutes, the solution is concentrated and the residue is recrystallized from acetone. There is obtained 2-[(2,6-difluorophenyl)imino]-1-hydroxyimidazolidine hydrobromide of melting point 225° (decomposition).

(d) From 2-[(2,6-difluorophenyl)imino]-1-hydroxyimidazolidine and 2-chloromethyl-pyridine N-oxide there is obtained, in analogy to the details in Example 1,2-([{2-[(2,6-difluorophenyl)imino]-1-imidazolidinyl}-oxy]methyl)-pyridine 1-oxide dihydrochloride of melting point 188°–189° (acetone/hydrogen chloride in dioxane).

EXAMPLE 4

Preparation of
2-([{2-[(2-chloro-5-methoxyphenyl)imino]-1-imidazolidinyl}oxy]-methyl)pyridine 1-oxide dihydrobromide (a) In analogy to the details in Example 3a, from 2-chloro-5-methoxyphenylisothiocyanate and N-{2-[N-(benzyloxy)amino]ethyl}phthalimide there is obtained 1-(benzyloxy)-3-(2-chloro-5-methoxyphenyl)-1-(2-phthalimidoethyl)-2-thiourea of melting point 138°–139° (methylene chloride/ether).

(b) From the above substance there is obtained, in analogy to the details in Example 3b, 1-(benzyloxy)-2-[(2-chloro-5-methoxyphenyl)imino]imidazolidine hydrochloride of melting point 198°–200° (acetone/hydrogen chloride in dioxane).

(c) A solution of 1.84 g of 1-(benzyloxy)-2-[(2-chloro-5-methoxyphenyl)imino]imidazolidine in 10 ml of ethanol and 0.65 ml of 25 percent hydrochloric acid is hydrogenated over palladium/carbon. The catalyst is subsequently removed by filtration and the solution obtained is evaporated in vacuo. There is obtained 2-[(2-chloro-5-methoxyphenyl)imino]-1-hydroxyimidazolidine hydrochloride of melting point 182°–184° (acetone).

(d) From 2-[(2-chloro-5-methoxyphenyl)imino]-1-hydroxyimidazolidine and 2-chloromethyl-pyridine N-oxide there is obtained, in analogy to the details in Example 1, 2-([{2-[(2-chloro-5-methoxyphenyl)imino]-1-imidazolidinyl}oxy]methyl)pyridine 1-oxide dihydrobromide of melting point 167°–168° (methanol/acetone).

EXAMPLE 5

Preparation of
2-([{2-[(2,6-dichloro-3-methoxyphenyl)-imino]-1-imidazolidinyl}oxy]-methyl)pyridine 1-oxide (a) A solution of 155.4 g of 2,4-dichloro-3-nitrophenol in 2 l of methylene chloride is treated with 16.9 g of benzyltrimethylammonium chloride. There is added thereto a solution of 44.8 g of sodium hydroxide in 1.8 l of water and, while stirring vigorously, 143 ml of dimethyl sulfate. After 1 hour, the organic phase is separated, washed with water, dried and evaporated in vacuo. There is obtained 2,4-dichloro-3-nitroanisole of melting point 97°–99° (hexane).

(b) A solution of 62.4 g of 2,4-dichloro-3-nitroanisole in 750 ml of ethanol is treated with 19 g of Raney-nickel and hydrogenated for 8 hours. The obtained solution is filtered and evaporated in vacuo. The residue is taken up in methylene chloride and the solution is washed with a dilute sodium carbonate solution. After drying the organic phase over sodium sulfate and evaporating in vacuo, there is obtained 2,6-dichloro-3-methoxyaniline of boiling point 84° (0.1 Torr).

(c) 60.7 g of 2,6-dichloro-3-methoxy-aniline are dissolved in 65 ml of toluene and treated with 25 ml of thiophosgene in 50 ml of toluene. The solution obtained is heated to boiling under reflux overnight and subsequently evaporated in vacuo. There is obtained 2,6-dichloro-3-methoxyphenylisothiocyanate of boiling point 99° (0.13 Torr).

(d) 23.4 g of 2,6-dichloro-3-methoxyphenylisothiocyanate and 29.0 g of N-[2-(benzyloxy)-amino)ethyl]phthalimide are heated to boiling under reflux with 150 ml of toluene for 5 hours. The obtained precipitate is removed by filtration under suction and dried. There is obtained 1-(benzyloxy)-3-(2,6-dichloro-3-methoxyphenyl)-1-(2-phthalimidoethyl)-2-thiourea of melting point 175°–176°.

(e) 42.0 g of 1-(benzyloxy)-3-(2,6-dichloro-3-methoxyphenyl)-1-(2-phthalimidoethyl)-2-thiourea and 20.6 g of triethyloxonium tetrafluoroborate are dissolved in 500 ml of methylene chloride and left to stand at room temperature for 2 hours. This solution is washed with a saturated sodium carbonate solution and with water, dried over sodium sulfate and evaporated in vacuo. There is obtained 3-(benzyloxy)-1-(2,6-dichloro-3-methoxy-phenyl)-2-ethyl-3-(2-phthalimidoethyl-2-thiopseudourea of melting point 121°–122° (isopropyl ether).

(f) A mixture of 46.0 g of 3-(benzyloxy)-1-(2,6-dichloro-3-methoxyphenyl)-2-ethyl-3-(2-phthalimidoethyl)-2-thiopseudourea, 100 ml of ethanol and 300 ml of a 40 percent solution of methylamine in water is stirred overnight at room temperature. The solution is heated to 50° for 2 hours, cooled down and extracted with ether. The organic phase is dried and evaporated in vacuo. The residue is taken up in 250 ml of toluene. The solution obtained is heated to boiling overnight, cooled down, washed with 3 N sodium hydroxide and with water, dried over sodium sulfate and evaporated in vacuo. A portion of the residual oil is dissolved in acetone and treated with hydrogen chloride in dioxane. There is obtained 1-(benzyloxy)-2-(2,6-dichloro-3-methoxyphenyl)imino-imidazolidine dihydrochloride of melting point 222°–223° (methanol/acetonitrile).

(g) A solution of 20.14 g of 1-(benzyloxy)-2-(2,6-dichloro-3-methoxyphenyl)imino-imidazolidine in 100 ml of ethanol is treated with 6.5 ml of concentrated hydrochloric acid and 1.0 g of palladium/carbon and hydrogenated at room temperature. After 2 hours, the solution is filtered and the filtrate is evaporated in vacuo. The residual material is taken up in acetone and heated to boiling under reflux. There is obtained 2-[(2,6-dichloro-3-methoxyphenyl)imino]-1-hydroxyimidazolidine hydrochloride of melting point 215°–217°.

(h) 19.0 g of 2-[2,6-dichloro-3-methoxyphenyl)imino]-1-hydroxyimidazolidine hydrochloride are suspended in 160 ml of toluene. There are added thereto successively 40 ml of a 40 percent solution of tetra-n-butylammonium hydroxide, 12.2 g of 2-chloromethyl-pyridine N-oxide and 250 ml of a saturated potassium carbonate solution. After 4 hours, the precipitated material is removed by filtration, washed with water and subsequently with ether and recrystallized from chloroform and ethanol. There is obtained 2-([{2-[(2,6-dichloro-3-methoxyphenyl)-imino]-1-imidazolidinyl}-oxy]methyl)-pyridine 1-oxide of melting point 199°–200° C. The corresponding dihydrobromide melts with decomposition at 192° (methanol/acetonitrile).

EXAMPLE 6

Preparation of
2-([{2-[(2,6-dichloro-4-methoxyphenyl)imino]-1-imidazolidinyl}-oxy]methyl)pyridine 1-oxide (a) 57.6 g of 2,6-dichloro-4-methoxy-aniline are added portionwise within 10 minutes to a stirred mixture, cooled in ice, of 27.6 g of formic acid and 61.2 g of acetic acid anhydride. The solid reaction mixture is diluted with 50 ml of formic acid and filtered. The precipitate is taken up in ethyl acetate. The organic solution is washed successively with ice-water, 3 N hydrochloric acid and saturated sodium carbonate solution, dried and evaporated in vacuo. After recrystallization of the residue from ethyl acetate, there is obtained 2,6-dichloro-4-methoxyformanilide of melting point 152°–153°.

(b) A solution of 59.3 g of 2,6-dichloro-4-methoxyformanilide in 600 ml of absolute methylene chloride is treated with 54.6 g of triethylamine. While cooling there are added dropwise at 20° within 30 minutes 200 ml of a 20 percent phosgene solution in toluene. The mixture is stirred for an additional 30 minutes at room temperature, the yellow suspension is treated with 600 ml of absolute methylene chloride and made basic with gaseous ammonia while cooling. The suspension is filtered and evaporated. The residue is treated with 300 ml of absolute tetrahydrofuran, filtered and again evaporated. After recrystallization from methylene chloride/hexane, there is obtained 2,6-dichloro-4-methoxyphenyl-isocyanide of melting point 110°–112°.

(c) A solution of 44 g of 2,6-dichloro-4-methoxyphenyl-isocyanide in 250 ml of dry tetrahydrofuran is treated at 20° over a period of 15 minutes with a solution of 83 g of phenyltrimethylammonium bromide dibromide. After evaporation of the yellow-red solution, there is obtained 2,6-dichloro-N-(dibromomethylene)-p-anisidine as a red-brown oil which is used in the next step without additional purification.

(d) A suspension of 52.6 g of N-(benzyloxy)-ethylenediamine dihydrochloride in 200 ml of water is treated portionwise with 76 g of potassium carbonate. While cooling and stirring well there is added dropwise thereto at 15° a solution of 80 g of 2,6-dichloro-N-(dibromoethylene)-p-anisidine in 100 ml of dry tetrahydrofuran. Thereafter, the suspension is poured into ice and extracted with ether. The organic phase is washed with a saturated sodium chloride solution, dried and evaporated. By treating the oil obtained with ether, there is obtained 1-(benzyloxy)-2-[(2,6-dichloro-4-methoxyphenyl)imino]imidazoline of melting point 90°–92°.

(e) 44.3 g of 1-(benzyloxy)-2-[(2,6-dichloro-4-methoxyphenyl)imino]imidazoline are dissolved in 350 ml of ethanol and 350 ml of acetic acid and treated with 13.8 ml of benzyl chloride. The mixture is hydrogenated in the presence of 1 g of platinum oxide under normal pressure. After completion of the hydrogen uptake, the catalyst is removed by filtration and the solution is evaporated. The residue is treated with water and washed with ether. The aqueous phase is made alkaline and extracted with ethyl acetate. After drying and evaporating the organic extracts and recrystallization of the residue from ethyl acetate/methanol, there is obtained 2-[(2,6-dichloro-4-methoxyphenyl)imino]-1-hydroxyimidazolidine of melting point 199°–201°.

(f) From 2-[(2,6-dichloro-4-methoxyphenyl)imino]-1-hydroxyimidazolidine and 2-chloromethyl-pyridine N-oxide there is obtained, in analogy to the details in Example 1, 2-([{2-[(2,6-dichloro-4-methoxyphenyl)imino]-1-imidazolidinyl}oxy]methyl)pyridine 1-oxide of melting point 184°–186° (methanol).

EXAMPLE 7

Preparation of 4-chloro-3-{[1-(2'-pyridylmethoxy)-2-imidazolidinylidene]amino}phenol 1'-oxide dihydrobromide 7.3 g of 2-([{2-[(2-chloro-5-methoxyphenyl)imino]-1-imidazolidinyl}oxy]methyl)pyridine 1-oxide are dissolved in 150 ml of 48 percent hydrobromic acid and heated to boiling under reflux for 2 hours. After cooling to room temperature, the precipitate is removed by filtration under suction, washed with a small amount of ethanol and dried in vacuo. The 4-chloro-3-{[1-(2'-pyridylmethoxy)-2-imidazolidinylidene]amino}phenol 1'-oxide dihydrobromide melts with decomposition at 214°–216°.

EXAMPLE 8

Preparation of 2,4-dichloro-3-{[1-(2'-pyridylmethoxy)-2-imidazolidinylidene]imino}-phenol 1'-oxide dihydrobromide In analogy to the details in Example 7, from 2-[{2-(2,6-dichloro-3-methoxyphenyl)imino-1-imidazolidinyl]oxy}methyl]pyridine 1-oxide and 48 percent hydrobromic acid there is obtained 2,4-dichloro-3-{[1-(2'-pyridylmethoxy)-2-imidazolidinylidene]imino}phenol 1'-oxide dihydrobromide of melting point 196°–197° (decomposition; methanol/acetone).

EXAMPLE 9

Preparation of 3,5-dichloro-4-{[1-(2'-pyridylmethoxy)-2-imidazolidinylidene]imino}-phenol 1'-oxide From 2-([{2-[(2,6-dichloro-4-methoxyphenyl)imino]-1-imidazolidinyl}oxy]methyl)pyridine 1-oxide and 48 percent hydrobromic acid there is obtained, in analogy to the details in Example 7, 3,5-dichloro-4-{[1-(2'-pyridylmethoxy)-2-imidazolidinylidene]imino}phenol 1'-oxide of melting point 208°–210° (48 percent hydrobromic acid).

EXAMPLE 10

Preparation of 1-acetyl-2-[(2,6-dichlorophenyl)imino]-3-(2'-pyridylmethoxy)imidazolidine 1'-oxide (a) A solution of 4.2 g of 2-([{2-[(2,6-dichlorophenyl)imino]-1-imidazolidinyl}oxy]-methyl)pyridine in 25 ml of acetic acid anhydride is heated at 55° for 2 hours and subsequently evaporated in vacuo. The residue is taken up in ether. The ethereal phase is extracted with a saturated sodium bicarbonate solution, dried and evaporated in vacuo. There is obtained 1-acetyl-2-[(2,6-dichlorophenyl)imino]-3-(2-pyridylmethoxy)imidazolidine of melting point 104°–105° (isopropyl ether).

(b) 2.0 g of the above material are dissolved in 20 ml of chloroform and treated at room temperature with 1.3 g of m-chloroperbenzoic acid. After 2 hours, the solution is washed with a 5 percent sodium carbonate solution, dried over sodium sulfate and evaporated in vacuo. The residue is recrystallized from acetonitrile/methylene chloride. There is obtained 1-acetyl-2-[(2,6-dichlorophenyl)imino]-3-(2'-pyridylmethoxy)imidazolidine 1'-oxide of melting point 200°–202°.

EXAMPLE 11

705 mg of 1-acetyl-2-[(2,6-dichlorophenyl)imino]-3-(2'-pyridylmethoxy)imidazolidine 1'-oxide and 3 ml of 3 N hydrochloric acid are heated at 50° for 30 minutes. The solution is made basic with sodium hydroxide and extracted with ethyl acetate. The organic extracts are dried and evaporated in vacuo. The residue is recrystallized from acetonitrile. The 2-([{2-[(2,6-dichlorophenyl)imino]-1-imidazolidinyl}oxy]methyl)pyridine 1-oxide obtained melts at 185°–186°.

EXAMPLE 12

(a) 2.3 g of 2-([{2-[(2,5-dichlorophenyl)-imino]-1-imidazolidinyl}oxy]methyl)pyridine and 5.1 ml of formic acid are cooled to 5° and treated with 12.2 ml of acetic acid anhydride. The solution is warmed to room temperature and evaporated in vacuo. The residue is taken up in ether. The organic phase is washed with a saturated sodium bicarbonate solution, dried and evaporated in vacuo. The residual of oil is chromatographed on silica gel with a mixture of 4 parts of chloroform and 1 part of ethyl acetate as the elution agent. There is obtained crystalline 2-[(2,5-dichlorophenyl)amino]-1-formyl-3-(2-pyridylmethoxy)imidazolidine of melting point 91°–92° (isopropyl ether).

(b) In analogy to the details in Example 10b, from 2-[(2,5-dichlorophenyl)imino]-1-formyl-3-(2-pyridylmethoxy)imidazolidine and m-chloroperbenzoic acid there is obtained 2-[(2,5-dichlorophenyl]imino]-1-formyl-3-(2'-pyridylmethoxy)imidazolidine 1'-oxide of melting point 146°–148° (acetone).

EXAMPLE 13

A solution of 0.4 g of 2-[(2,5-dichlorophenyl)imino]-1-formyl-3-(2'-pyridylmethoxy)-imidazolidine 1'-oxide in 5 ml of ethanol is treated with 3 ml of 3 N sulfuric acid, left to stand at room temperature for 2 days, made basic with a saturated sodium bicarbonate solution and extracted with methylene chloride. The organic solution is dried and evaporated in vacuo. The 2-([{2-[(2,5-dichlorophenyl)imino]-1-imidazolidinyl}oxy]methyl)-pyridine 1-oxide obtained by recrystallization of the residue from acetonitrile melts at 167°–168°.

EXAMPLE 14

Preparation of
2-[(6-chloro-o-tolyl)imino]-1-formyl-3-(2'-pyridylmethoxy)imidazolidine 1'-oxide (a) In analogy to the details in Example 12a, from 2-([{2-[(6-chloro-o-tolyl)imino]-1-imidazolidinyl}oxy]-methyl)pyridine, formic acid and acetic acid anhydride there is obtained 2-[(6-chloro-o-tolyl)imino]-3-(2-pyridylmethoxy)-1-imidazolidine-carboxaldehyde of melting point 63°–64° (isopropyl ether).

(b) From 2-[(6-chloro-o-tolyl)imino]-3-(2-pyridylmethoxy)-1-imidazolidine-carboxaldehyde and m-chloroperbenzoic acid there is obtained, in analogy to the details in Example 10b, 2-[(6-chloro-o-tolyl)imino]-1-formyl-3-(2'-pyridylmethoxy)imidazolidine 1'-oxide of melting point 166°–167° (acetone).

EXAMPLE 15

From 2-[(6-chloro-o-tolyl)imino]-1-formyl-3-(2'-pyridylmethoxy)imidazolidine 1'-oxide there is obtained, in analogy to the details in Example 13, 2-[(6-chloro-o-tolyl)imino]-3-(2'-pyridylmethoxy)imidazolidine 1'-oxide dihydrochloride of melting point 171°–173° (dioxane/acetone).

EXAMPLE 16

(a) A solution of 16.8 g of 1-(benzyloxy)-2-[(2,6-dichlorophenyl)imino]imidazolidine in 150 ml of dry methanol is treated with 5.83 g of sodium carbonate and 7.81 g of methyl iodide. The mixture is heated to reflux while stirring for 4 hours and then evaporated in vacuo. The residue is partitioned between water and methylene chloride. The organic phase is dried and evaporated. The residual oil is chromatographed on silica gel while eluting with a mixture of chloroform and ethanol (9:1). There is obtained an oil which is dissolved in acetone and treated with hydrogen chloride in dioxane and then with ether until turbidity occurs. The 1-(benzyloxy)-2-(2,6-dichloro-N-methylanilino)-2-imidazoline hydrochloride obtained melts at 185°–186°.

(b) 12.6 g of the corresponding free base are heated at 150° for 1 hour with 70 ml of 48 percent hydrobromic acid. To the cooled solution are added a small amount of ice and a spatula tip of Norit. The solution is filtered and made basic with concentrated ammonia. The precipitate which thus results is removed by filtration under suction, washed with water and recrystallized from methanol/acetonitrile. The 2-(2,6-dichloro-N-methylanilino)-1-hydroxy-2-imidazoline melts at 177°–178° with decomposition.

(c) From 2-(2,6-dichloro-N-methylanilino)-1-hydroxy-2-imidazoline and 2-chloromethyl-pyridine N-oxide there is obtained in analogy to the details in Example 1, 2-[{[2-(2,6-dichloro-N-methylanilino)-2-imidazolin-1-yl]oxy}-methyl]pyridine 1-oxide dihydrochloride of melting point 156°–157°.

EXAMPLE 17

Preparation of
2-[{[2-(N-allyl-2,6-dichloroanilino)-1-imidazolin-1-yl]oxy}methyl]-pyridine 1-oxide (a) 9.9 g of 1-(benzyloxy)-2-[(2,6-dichlorophenyl)imino]imidazolidine, 1.0 g of tetra-n-butylammonium sulfate and 5.0 ml of allyl bromide are heated at 100° with 35 ml of water for 20 minutes. The mixture obtained is treated with a saturated sodium carbonate solution and extracted with ether. The organic phase is dried and evaporated in vacuo. The residual oily 2-(N-allyl-2,6-dichloroanilino)-1-(benzyloxy)-2-imidazoline is used in the next step without further purification.

(b) 9.0 g of 2-(N-allyl-2,6-dichloroanilino)-1-(benzyloxy)-2-imidazoline are dissolved in 200 ml of methylene chloride and cooled down to −40°. There is added thereto dropwise a solution of 14.5 g of boron trichloride in 200 ml of methylene chloride. The mixture is left to warm to room temperature and the solution is evaporated in vacuo. The residue is treated with a saturated sodium carbonate solution and methylene chloride. The resulting precipitate is removed by filtration and recrystallized from methanol. There is thus obtained 2-(N-allyl-2,6-dichloroanilino)-1-hydroxy-2-imidazoline of melting point 204° (decomposition).

(c) From 2-(N-allyl-2,6-dichloroanilino)-1-hydroxy-2-imidazoline and 2-chloromethyl-pyridine N-oxide there is obtained, in analogy to the details in Example 1, 2-[{[2-(N-allyl-2,6-dichloroanilino)-1-imidazolin-1-yl]oxy}methyl]-pyridine 1-oxide of melting point 116°–117° (isopropyl ether).

EXAMPLE 18

Preparation of
2-([{2-[(2,6-dichlorophenyl)imino]-3-methyl-1-imidazolidinyl}oxy]methyl)-pyridine 1-oxide dihydrochloride (a) 16.8 g of 1-(benzyloxy)-2-[(2,6-dichlorophenyl)imino]-imidazolidine are dissolved in 80 ml of dimethylformamide and treated while stirring at room temperature with 1.44 g of sodium hydride. After 1 hour, there is added dropwise thereto a solution of 4 ml of methyl iodide in 20 ml of toluene. The temperature rises to 48°.

After 16 hours, the mixture is poured into ice and extracted with ether. The organic phase is washed successively with water, 15 percent tartaric acid solution and water, dried over magnesium sulfate and evaporated in vacuo. The 1-(benzyloxy)-2-[(2,6-dichlorophenyl)imino]-3-methylimidazolidine obtained is used in the next step without further purification.

(b) 20.6 g of 1-(benzyloxy)-2-[(2,6-dichlorophenyl)imino]-3-methylimidazolidine are warmed at 150° with 100 ml of 48 percent hydrobromic acid. After 1 hour, the solution is poured into ice, treated with Norit and filtered. The filtrate is made basic with concentrated ammonia. The resulting precipitate is removed by filtration under suction, washed with water and dried. The 2-[(2,6-dichlorophenyl)imino]-1-hydroxy-3-methylimidazolidine melts at 187°–189° (decomposition).

(c) From 2-[(2,6-dichlorophenyl)imino]-1-hydroxy-3-methylimidazolidine and 2-chloromethyl-pyridine N-oxide there is obtained, in analogy to the details in example 1, 2-([{2-[(2,6-dichlorophenyl)imino]-3-methyl-1-imidazolidinyl}oxy]methyl)pyridine 1-oxide dihydrochloride of melting point 177°–178° (acetone/hydrogen chloride in dioxane).

EXAMPLE 19

Preparation of
2-[{[2-(o-tolyl-imino)-1-imidazolidinyl]oxy}methyl]-pyridine 1-oxide dihydrobromide (a) A suspension of 21.6 g of N-(benzyloxy)ethylenediamine dihydrochloride in 250 ml of toluene is treated with 18.8 g of o-tolylimidocarbonyl chloride, 3.4 g of tetra-n-butylammonium hydrogen sulfate and, while stirring vigorously, dropwise with 80 ml of 28 percent sodium hydroxide. In so doing, the temperature rises to 52°. The mixture is stirred overnight and diluted with ether. The organic phase is separated, washed with water and extracted three times with 3 N sulfuric acid. The aqueous-acidic phase is made alkaline with concentrated sodium hydroxide and extracted with ether. The ethereal solution is dried and evaporated in vacuo. There is obtained 1-(benzyloxy)-2-[(o-tolyl)imino]imidazolidine as a viscous oil which is used directly in the next step.

(b) 22.5 g of 1-(benzyloxy)-2-[(o-tolyl)imino]imidazolidine are heated at 150° for 30 minutes with 150 ml of 48 percent hydrobromic acid. The mixture is evaporated in vacuo. From the residue there is obtained 1-hydroxy-2-(o-tolylimino)imidazolidine hydrobromide of melting point 176°–187° (acetone).

(c) From 1-hydroxy-2-(o-tolylimino)imidazolidine and 2-chloromethyl-pyridine N-oxide there is obtained, in analogy to the details in Example 1, 2-[{[2-(o-tolylimino)-1-imidazolidinyl]oxy}methyl]pyridine 1-oxide dihydrobromide of melting point 195°–196° (methanol/acetone).

EXAMPLE 20

Preparation of
2-([{2-[(2,6-diethylphenyl)imino]-1-imidazolidinyl}oxy]methyl)-pyridine 1-oxide (a) In analogy to the details in Example 19a, from (2,6-diethylphenyl)imidocarbonyl chloride and N-(benzyloxy)-ethylenediamine dihydrochloride there is obtained 1-(benzyloxy)-2-[(2,6-diethylphenyl)imino]imidazolidine as an oil.

(b) In analogy to the details in Example 19b, from 1-(benzyloxy)-2-[(2,6-diethylphenyl)imino]imidazolidine and hydrobromic acid there is obtained 2-[(2,6-diethylphenyl)imino]-1-hydroxyimidazolidine hydrobromide of melting point 129°–130° (acetonitrile/ether).

(c) From 2-[(2,6-diethylphenyl)imino]-1-hydroxyimidazolidine and 2-chloromethyl-pyridine N-oxide there is obtained, in analogy to the details in Example 1, 2-([{2-[(2,6-diethylphenyl)imino]-1-imidazolidinyl}oxy]methyl)-pyridine 1-oxide of melting point 124°–125° (acetonitrile).

EXAMPLE 21

Preparation of
2-[(2,6-dichlorophenyl)imino]-3-[(6'-methyl-2'-pyridyl)-methoxy]-1-imidazolidine carboxaldehyde 1'-oxide (a) From 2-([{2-[(2,6-dichlorophenyl)imino]-1-imidazolidinyl}oxy]methyl)-6-methyl-pyridine, formic acid and acetic acid anhydride there is obtained, in analogy to the details in Example 12a, 2-[(2,6-dichlorophenyl)imino]-3-[(6-methyl-2-pyridyl)methoxy]-1-imidazolidine-carboxaldehyde of melting point 85°–86° (isopropyl ether).

(b) From 2-[(2,6-dichlorophenyl)imino]-3-[(6-methyl-2-pyridyl)methoxy]-1-imidazolidine-carboxaldehyde and m-chloroperbenzoic acid there is obtained, in analogy to the details in Example 10b, 2-[(2,6-dichlorophenyl)imino]-3-[(6'-methyl-2'-pyridyl)methoxy]-1-imidazolidine-carboxaldehyde 1'-oxide of melting point 159°–160° (acetone).

EXAMPLE 22

Preparation of
2-([{2-[(2,6-dichlorophenyl)imino]-1-imidazolidinyl}oxy]-methyl)-6-methylpyridine 1-oxide From 2-[(2,6-dichlorophenyl)imino]-1-formyl-3-[2'-(6'-methyl)pyridylmethoxy) imidazolidine 1'-oxide there is obtained, in analogy to the details in Example 13, 2-([{2-[(2,6-dichlorophenyl)imino]-1-imidazolidinyl}oxy]-methyl)-6-methylpyridine 1-oxide of melting point 196°–197° (methanol/acetone).

EXAMPLE 23

Preparation of
1-acetyl-2-[(2,6-dichlorophenyl)imino]-3-(2'-pyridylmethoxy)imidazolidine 1'-oxide A suspension of 3.5 g of 2-([{2-[(2,6-dichlorophenyl)imino]-1-imidazolidinyl}-oxy]methyl)pyridine 1-oxide and 20 ml of acetic acid anhydride is stirred at 55° for 10 hours. After cooling, the precipitated crystals are removed by filtration under suction and washed with cyclohexane. There is obtained 1-acetyl-2-[(2,6-dichlorophenyl)imino]-3-(2'-pyridylmethoxy)imidazolidine 1'-oxide of melting point 200°–202° (methylene chloride/acetonitrile).

EXAMPLE 24

Preparation of
2-([{2-[(2,6-dichlorophenyl)imino]-1-imidazolidinyl}oxy]-methyl)-6-methoxypyridine 1-oxide From 2-[(2,6-dichlorophenyl)imino]-1-hydroxyimidazolidine and 2-(chloromethyl)-6-methoxypyridine 1-oxide there is obtained, in analogy to the details in Example 1, 2-([{2-[2,6-dichlorophenyl)imino]-1-imidazolidinyl}oxy]methyl)-6-methoxypyridine 1-oxide of melting point 184°–185° (acetonitrile/isopropyl ether).

EXAMPLE 25

Preparation of
2-([{2-[(2,6-dichlorophenyl)imino]-1-imidazolidinyl}oxy]-methyl)-3-methoxypyridine 1-oxide dihydrobromide From 2-[(2,6-dichlorophenyl)imino]-1-hydroxyimidazolidine and 2-(chloromethyl)-3-methoxypyridine 1-oxide hydrochloride there is obtained, in analogy to the details in Example 1, 2-([{2-[(2,6-dichlorophenyl)imino]-1-imidazolidinyl}oxy]methyl)-3-methoxypyridine 1-oxide dihydrobromide of melting point 156°–157° (decomposition; methanol/acetone).

EXAMPLE 26

Preparation of
2-[(2,6-dichlorophenyl)-imino]-3-[(4'-methoxy-2'pyridyl)methoxy]-1-imidazolidine-carboxaldehyde 1'-oxide (a) In analogy to the details in Example 1, from 2-[(2,6-dichlorophenyl)imino]-1-hydroxyimidazolidine and 2-(chloromethyl)-4-methoxypyridine hydrochloride there is obtained 2-([{2-[(2,6-dichlorophenyl)imino]-1-imidazolidinyl}-oxy]methyl)-4-methoxypyridine of melting point 127°–128° (acetonitrile).

(b) In analogy to the details in Example 12a, from 2-([{2-[(2,6-dichlorophenyl)imino]-1-imidazolidinyl}oxy]-methyl)-4-methoxypyridine, formic acid and acetic acid anhydride there is obtained 2-[(2,6-dichlorophenyl)imino]-3-[(4-methoxy-2-pyridyl)methoxy]-1-imidazolidine-carboxaldehyde of melting point 134°–135° (methylene chloride/isopropyl ether).

(c) In analogy to the details in Example 10b, from 2-[(2,6-dichlorophenyl)imino]-3-[(4-methoxy-2-pyridyl)-methoxy]-1-imidazolidine-carboxaldehyde and m-chloroperbenzoic acid there is obtained 2-[(2,6-dichlorophenyl)-imino]-3-[(4'-methoxy-2'pyridyl)methoxy]-1-imidzolidine-carboxaldehyde 1'-oxide of melting point 175°–176° (methylene chloride/acetonitrile).

EXAMPLE 27

Preparation of
2-([{2-[(2,6-dichlorophenyl)imino]-1-imidazolidinyl}oxy]methyl)-4-methoxypyridine-1-oxide In analogy to the details in Example 13, from 2-[(2,6-dichlorophenyl)imino]-3-[(4'-methoxy-2'-pyridyl)-methoxy]-1-imidazolidine-carboxaldehyde 1'-oxide and 3 N sulfuric acid there is obtained 2-([{2-[(2,6-dichlorophenyl)imino]-1-imidazolidinyl}oxy]methyl)-4-methoxypyridine 1-oxide of melting point 155°–157° (methylene chloride/acetonitrile).

EXAMPLE 28

Preparation of
2-([{2-[(2,6-dichlorophenyl)-imino]-1-imidazolidinyl}-oxy]methyl)-4-pyridinol 1-oxide dihydrochloride In analogy to the details in Example 7, from 2-([{2-[(2,6-dichlorophenyl)imino]-1-imidazolidinyl}oxy]-methyl)-4-methoxypyridine 1-oxide and 48 percent hydrobromic acid there is obtained 2-([{2-[(2,6-dichlorophenyl)-imino]-1-imidazolidinyl}oxy]methyl)-4-pyridinol 1-oxide dihydrochloride of melting point 182° (decomposition; acetone/dioxan/hydrogen chloride).

EXAMPLE 29

Preparation of
6-([{2-[(2,6-dichlorophenyl)-imino]-1-imidazolidinyl}-oxy]methyl)-2-pyridinol 1-oxide hydrobromide In analogy to the details in Example 7, from 2-([{2-(2,6-dichlorophenyl)imino]-1-imidazolidinyl}oxy]methyl)-6-methoxypyridine 1-oxide and 48 percent hydrobromic acid there is obtained 6-([{2-[(2,6-dichlorophenyl)-imino]-1-imidazolidinyl}oxy]methyl)-2-pyridinol 1-oxide hydrobromide of melting point 156°–158° (48 percent hydrobromic acid).

EXAMPLE 30

Preparation of
2-[(2,6-dichlorophenyl)-imino]-3-[(5'-methoxy-2'-pyridyl)methoxy]-1-imidazolidine-carboxaldehyde 1'-oxide (a) In analogy to the details in Example 1, from 2-[(2,6-dichlorophenyl)imino]-1-hydroxyimidazolidine and 2-(chloromethyl)-5-methoxypyridine hydrochloride there is obtained 2-([{2-[(2,6-dichlorophenyl)imino]-1-imidazolidinyl}oxy]-methyl)-5-methoxypyridine dihydrochloride of melting point 107°–108° (acetonitrile/isopropyl ether).

(b) In analogy to the details in Example 12a, from 2-([{2-[(2,6-dichlorophenyl)imino]-1-imidazolidinyl}oxy]-methyl)-5-methoxypyridine, formic acid and acetic acid anhydride there is obtained 2-[(2,6-dichlorophenyl)imino]-3-[(5-methoxy-2-pyridyl)methoxy]-1-imidazolidine-carboxaldehyde of melting point 126°–127° (acetonitrile).

(c) In analogy to the details in Example 10b, from 2-[(2,6-dichlorophenyl)imino]-3-[(5-methoxy-2-pyridyl)-methoxy]-1-imidazolidine-carboxaldehyde and m-chloroperbenzoic acid there is obtained 2-[(2,6-dichlorophenyl)-imino]-3-[(5'-methoxy-2'-pyridyl)methoxy]-1-imidazolidine-carboxaldehyde 1'-oxide of melting point 148°–149° (acetonitrile).

EXAMPLE 31

Preparation of
2-([{2-[(2,6-dichlorophenyl)imino]-1-imidazolidinyl}oxy]methyl)-5-methoxy-pyridine 1-oxide dihydrochloride In analogy to the details in Example 13, from 2-[(2,6-dichlorophenyl)imino]-3-[(5'-methoxy-2'-pyridyl)-methoxy]-1-imidazolidine-carboxaldehyde 1'-oxide and 3 N sulfuric acid there is obtained 2-([{2-(2,6-dichlorophenyl)imino]-1-imidazolidiny}oxy]methyl)-5-methoxy-pyridine 1-oxide dihydrochloride of melting point 171°–172° (decomposition; acetonitrile).

EXAMPLE 32

Preparation of
6-([{2-[(2,6-dichlorophenyl)imino]-1-imidazolidinyl}oxy]methyl)-3-pyridinol 1-oxide dihydrobromide In analogy to the details in Example 7, from 2-([{2-[(2,6-dichlorophenyl)imino]-1-imidazolidinyl}oxy]methyl)-5-methoxypyridine 1-oxide dihydrochloride and 48 percent hydrobromic acid there is obtained 6-([{2-[(2,6-dichlorophenyl)imino]-1-imidazolidinyl}-oxy]methyl)-3-pyridinol 1-oxide dihydrobromide of melting point 232° (decomposition; ethanol/acetone).

EXAMPLE 33

Preparation of 2-([{2-[(2,6-dichlorophenyl)imino]-1-imidazolidinyl}oxy]methyl)-3-pyridinol 1-oxide dihydrobromide In analogy to the details in Example 7, from 2-([{2-[(3,6-dichlorophenyl)imino]-1-imidazolidinyl}oxy]methyl)-3-methoxypyridine dihydrobromide and 48 percent hydrobromic acid there is obtained 2-([{2-[(2,6-dichlorophenyl)imino]-1-imidazolidinyl}oxy]methyl)-3-pyridinol 1-oxide dihydrobromide of melting point 193°–195° (decomposition acetone).

Example A

Preparation of coated tablets of the following composition described below:

| | | |
|---|---|---|
| 2-([{2-[(2,6-Dichlorophenyl)imino]-1-imidazolidinyl}oxy]methyl)pyridine 1-oxide N—cyclohexylsulfamate | | 5.32 mg |
| Lactose (powered) | | 34.68 mg |
| Maize starch (white) | | 59.0 mg |
| Talc | | 0.5 mg |
| Magnesium stearate | | 0.5 mg |
| | Nucleus weight | 100.0 mg |
| Dry coating substance | about | 7.0 mg |
| | Coated tablet weight about | 107.0 mg |

A mixture of the active substance with the powdered lactose and a portion of the maize starch is moistened with a paste made from an additional portion of the maize starch and water, kneaded, granulated, dried and sieved. This granulate is mixed with the remaining maize starch, the talc and the magnesium stearate and pressed to nuclei weighing 100 mg. The nuclei are coated with about 7.0 mg of dry coating substance using one of the known methods.

I claim:

1. A compound of the formula

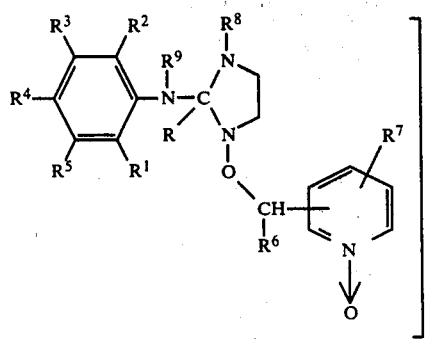

wherein $R^1$, $R^2$ and $R^3$, independently, are hydrogen, halogen trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl-(lower alkyl) or acyl and $R^9$ taken together with R is an additional bond, or $R^9$ is lower alkyl, lower alkenyl or aryl-(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, or a pharmaceutically acceptable acid addition salt thereof.

2. A compound in accordance with claim 1, wherein $R^7$ is hydrogen, lower alkyl or lower alkoxy.

3. A compound in accordance with claim 1, wherein $R^1$, $R^2$ and $R^3$, independently, are hydrogen, fluorine, chlorine, bromine, trifluoromethyl, methyl, ethyl or isopropyl.

4. A compound in accordance with claim 3, wherein one of $R^4$ and $R^5$ is hydrogen and the other is hydrogen, chlorine, hydroxy or methoxy.

5. A compound in accordance with claim 4, wherein $R^6$ is hydrogen or methyl.

6. A compound in accordance with claim 5, wherein $R^7$ is hydrogen, hydroxy, methyl or methoxy.

7. A compound in accordance with claim 6, wherein $R^8$ is hydrogen and $R^9$ together with R is an additional bond.

8. A compound in accordance with claim 7, wherein $R^1$ or $R^3$ is hydrogen and $R^2$ and $R^3$ or $R^1$ and $R^2$ are the same.

9. A compound in accordance with claim 8, wherein $R^2$ and $R^3$ or $R^1$ and $R^2$ is halogen.

10. A compound in accordance with claim 9, wherein $R^2$ and $R^3$ or $R^1$ and $R^2$ is chlorine.

11. A compound in accordance with claim 10, wherein $R^4$, $R^5$ and $R^8$ are hydrogen and $R^9$ taken together with R is an additional bond.

12. A compound in accordance with claim 1, 2-([{2-[(2,6-dichlorophenyl)-imino]-1-imidazolidinyl}-oxy]methyl)pyridine 1-oxide.

13. A compound in accordance with claim 1, 2-([{2-[(2,3-dichlorophenyl)imino]-1-imidazolidinyl}-oxy]methyl)pyridine 1-oxide.

14. A compound in accordance with claim 1, 2-[{(2-(2,6-Dichloro-N-methylanilino)-2-imidazolin-1-yl]oxy}methyl]pyridine 1-oxide.

15. A compound in accordance with claim 1, 2-([{2-[(2,6-dichlorophenyl)-imino]-1-imidazolidinyl}oxy]methyl)-4-methylpyridine 1-oxide.

16. A compound in accordance with claim 1, 4-(1-[{2-[(2,6-Dichlorophenyl)imino]-1-imidazolidinyl}oxy]ethyl)pyridine 1-oxide.

17. A compound in accordance with claim 1, 2-([{2-[(2,6-Dichlorophenyl)imino]-1-imidazolidinyl}oxy]methyl)-5-methylpyridine 1-oxide.

18. A compound in accordance with claim 1, 2-([{2-[(2,6-Dichlorophenyl)imino]-1-imidazolidinyl}oxy]methyl)-6-methylpyridine 1-oxide.

19. A compound in accordance with claim 1, 2-([{2-[(2,6-Dichlorophenyl)imino]-1-imidazolidinyl}oxy]methyl)-4-pyridinol 1-oxide.

20. A compound of the formula

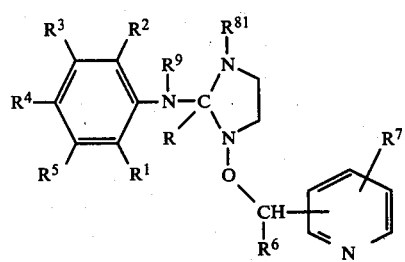

wherein $R^1$, $R^2$ and $R^3$, independently, are hydrogen, halogen, trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^{81}$ is lower alkyl, lower alkenyl, aryl-(lower alkyl) or acyl and $R^9$ taken together with R is an additional bond, or $R^9$ is lower alkyl, lower alkenyl or aryl-(lower alkyl) and $R^{81}$ taken together with R is an additional bond; provided that $R^4$ or $R^5$ is not hydroxy when $R^7$ is lower alkoxy and/or $R^{81}$ is acyl, and that $R^7$ is not hydroxy when $R^4$ or $R^5$ is lower alkoxy and/or $R^{81}$ is acyl.

21. A pharmaceutical composition containing a compound of the formula

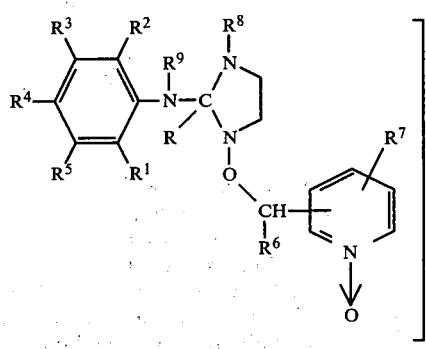

wherein $R^1$, $R^2$ and $R^3$, independently, are hydrogen, halogen, trifluoromethyl, nitro, lower alkyl or lower alkylthio, one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl-(lower alkyl) or acyl and $R^9$ taken together with R is an additional bond, or $R^9$ is lower alkyl, lower alkenyl or aryl-(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, or a pharmaceutically acceptable acid addition salt thereof, and an inert carrier material.

22. A pharmaceutical composition in accordance with claim 21, wherein the compound of Formula I is 2-([{2-[(2,6-dichlorophenyl)-imino]-1-imidazolidinyl}-oxy]-methyl)pyridine 1-oxide.

23. A method of controlling or preventing pain which comprises administering an effective amount of a compound of the formula

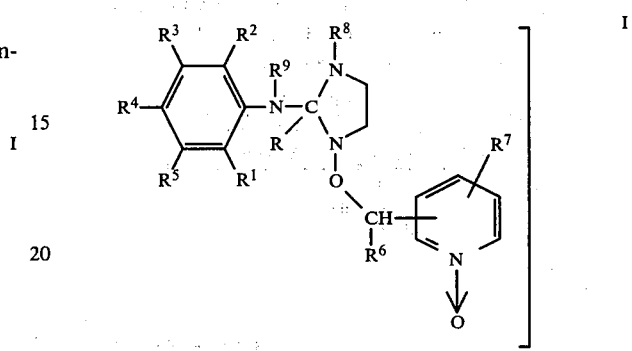

wherein $R^1$, $R^2$ and $R^3$, independently, are hydrogen, halogen, trifluoromethyl, nitro, lower alkyl or lower alkylthio; one of $R^4$ and $R^5$ is hydrogen and the other is hydrogen, halogen, hydroxy or lower alkoxy; $R^6$ is hydrogen or lower alkyl; $R^7$ is hydrogen, hydroxy, lower alkyl or lower alkoxy; and either $R^8$ is hydrogen, lower alkyl, lower alkenyl, aryl-(lower alkyl) or acyl and $R^9$ taken together with R is an additional bond, or $R^9$ is lower alkyl, lower alkenyl or aryl-(lower alkyl) and $R^8$ taken together with R is an additional bond; provided that $R^4$ or $R^5$ is not hydroxy when $R^7$ is lower alkoxy and/or $R^8$ is acyl, and that $R^7$ is not hydroxy when $R^4$ or $R^5$ is lower alkoxy and/or $R^8$ is acyl, or a pharmaceutically acceptable acid addition salt thereof.

24. A method in accordance with claim 23, wherein the compound of formula I is 2-([{2-[(2,6-dichlorophenyl)imino]-1-imidazolidinyl}oxy]methyl)pyridine 1-oxide.

* * * * *